United States Patent
Moo-Young et al.

[11] Patent Number: 6,117,441
[45] Date of Patent: *Sep. 12, 2000

[54] SILICONE CORE LONG TERM ANDROGEN DELIVERY IMPLANT

[75] Inventors: Alfred J. Moo-Young, Hastings-on-Hudson, N.Y.; Saleh I. Saleh, Assuit, Egypt

[73] Assignee: The Population Council, Inc., New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 09/109,760

[22] Filed: Jul. 2, 1998

[51] Int. Cl.[7] .............................. A61F 13/00; A61F 2/00; A61K 9/24; A61K 9/14
[52] U.S. Cl. .......................... 424/422; 424/486; 424/423; 424/473
[58] Field of Search ..................................... 424/422, 423, 424/424, 425

[56] References Cited

U.S. PATENT DOCUMENTS

| | | |
|---|---|---|
| 3,710,795 | 1/1973 | Higuchi et al. . |
| 3,832,252 | 8/1974 | Higuchi et al . |
| 3,854,480 | 12/1994 | Zaffaroni . |
| 4,052,505 | 10/1977 | Higuchi et al. ............................ 424/14 |
| 4,234,571 | 11/1980 | Nestor et al. . |
| 4,451,253 | 5/1984 | Harman ..................................... 604/60 |
| 4,957,119 | 9/1990 | De Nijs . |
| 5,028,430 | 7/1991 | Sanders et al. ........................ 424/423 |
| 5,035,891 | 7/1991 | Runkel et al. ........................... 424/423 |
| 5,088,505 | 2/1992 | De Nijs . |
| 5,266,325 | 11/1993 | Kuzma et al. . |
| 5,292,515 | 3/1994 | Moro et al. . |
| 5,660,848 | 8/1997 | Moo-Young et al. .................. 424/425 |
| 5,733,565 | 3/1998 | Moo-Young et al. . |

FOREIGN PATENT DOCUMENTS

| | | |
|---|---|---|
| 0 293 632 A1 | 12/1988 | European Pat. Off. . |
| 0 710 491 A1 | 5/1996 | European Pat. Off. . |

OTHER PUBLICATIONS

Sundaram et al., 7 Alpha–Methyl –Nortestosterone (MENT): the Optimal Androgen for Male Contracception, Annals of Medicine, 25:199–205, 1993.
Sundaram et al., *"Alpha–Methyl–Nortestosterone (MENT): The Optimal Androgen For Male Contraception"* Annals of Medicine, (1993), 25, 199–205.
Chien et al., J. Pharm. Sci 63, 365 (1974).
Shoupe et al., AM. J. Obstet. Gynecol., 160:1286–92 (1989).
Tikkanen et al., J. Reprod. Med., 31:898–905 (1986).

*Primary Examiner*—Thurman K. Page
*Assistant Examiner*—Todd Ware
*Attorney, Agent, or Firm*—Lerner, David, Littenberg, Krumholz & Mentlik, LLP

[57] ABSTRACT

This invention features an implantable system for use as a male contraception and as a treatment of benign prostate hypertrophy and other conditions. The implant system includes an implant intended for subcutaneous or local administration having a core comprising a silicone elastomer and drug matrix which is encased in an ethyl vinyl acetate coating or membrane.

21 Claims, 3 Drawing Sheets

SILICONE CORE LONG TERM ANDROGEN DELIVERY IMPLANT

Financial support for the invention described herein was received from the U.S. Agency for International Development under Cooperative Agreement No. DPE-3050-A-00-8059-00. Therefore, the U.S. Government may have certain rights in the invention.

FIELD OF THE INVENTION

The present invention relates to the field of male contraception as well as the treatment of benign prostate hypertrophy, and other conditions which can be treated by androgen or hormone therapy and to methods and apparatus for accomplishing same. More particularly, this invention relates to an improved implantable delivery system.

BACKGROUND OF THE INVENTION

Implantable or subcutaneous delivery devices have been known for the delivery of contraceptives in women for some time. Indeed, a number of devices have been used in subcutaneous contraception systems for women, including the much publicized NORPLANT® and NORPLANT II® systems. These systems involve implants composed of a silicone elastomer, such as, for example, SILASTIC®, siloxane-containing material available from Dow Corning. See U.S. Pat. Nos. 4,957,119 and 5,088,505. The convenience and reliability of these systems render them desirable substitutes for other forms of chemical and mechanical contraception.

Of course, if similar systems could be provided for men, their convenience might encourage a greater portion of the already sexually active population to engage in contraception. However, the production of a subcutaneous male contraceptive is not without difficulty. One cannot merely administer compounds which block gonadotrophin secretion and sperm production, such as LHRH and its analogues, without also decreasing testosterone production. This can depress male sexual function which would undermine the advantages of using this type of system. Therefore, androgens must be an essential part of an overall male subcutaneous contraceptive strategy.

One possible answer involves the production of an implant system for administering both an androgen and a sterilant. One implant would be administered to a patient and would deliver an androgen such as testosterone or 7α-methyl-19-nortestosterone ("MENT") or its acetate derivative ("MENT Ac") to provide for normal male function. The same implant or another implant would administer a sterilant. The NORPLANT® system would seem a likely model for such implants. Unfortunately, when these silicone-based implants were investigated, considerable complications arose. In fact, a system using a silicone elastomer-based implant was found to be unsatisfactory. As noted in Sundaram et al., "7 Alpha-Methyl-Nortestoster-one (MENT): The Optimal Androgen For Male Contraception," *Annals of Medicine*, (1993), 25, 199–205, SILASTIC® based implants containing MENT had to be replaced at intervals of three weeks because of the rapid loss of androgen. Based on this discovery, it was concluded that androgen could not be administered from silicone elastomer containing implants in a long-term, practical, highly repeatable fashion.

It was subsequently discovered that androgen could be delivered alone for androgen therapy when done as part of an implant system using an ethyl vinyl acetate ("EVA") core and an EVA containing rate limiting coating. See U.S. Pat. No. 5,733,565. Of course, while this discovery was a significant breakthrough in male contraception, it is still desirable to identify other implant systems which could be useful for the delivery of androgen, either alone as part of androgen replacement therapy or in combination with a sterilant to maintain male cell sex function while providing contraceptive efficacy.

SUMMARY OF THE INVENTION

While it was previously concluded that SILASTIC® and other silicone-based polymers should be avoided when constructing subcutaneous implants for the delivery of androgen, it has now been discovered that silicone elastomers such as SILASTIC® can play a role in the production of male contraceptive implants after all. Indeed, there are advantages to constructing an androgen containing implant from a core of a silicone elastomer so long as ethyl vinyl acetate or other suitable material is used as the rate limiting membrane surrounding the reservoir or core. These advantages include providing a sustained and constant release of a daily dose of a drug and having a near zero-order release rate profile. This result was particularly surprising in view of the original observation that exclusively silicone-based implants exhibited an unsatisfactory release rate profile. In addition, the availability of silicone elastomers as a core-forming materials provides significant benefits as silicone elastomers may have enhanced compatibility with specific androgens and their analogues. Because silicone elastomers can be modified to provide properties which are different than ethyl vinyl acetate monomers, it may be possible to affect the properties of the core by the use of one or another specific material. Adding SILASTIC® or silicone elastomers to the arsenal of potential core source materials is therefore of great benefit.

In accordance with one aspect of the present invention, there is provided a subcutaneous implant for the delivery of androgen. The implant includes a core comprising a silicone elastomer and drug matrix encased in a rate limiting EVA coating or membrane. This device may be used alone for hormone replacement therapy and to treat various conditions for which androgen therapy is a recognized treatment.

In a particularly preferred embodiment in accordance with the present invention, this silicone elastomeric cored implant can be used in combination with a suitable implant for the delivery of a sterilant such as LHRH, its analogues or functionally related compounds. In this instance, by the use of two implants, for example, both contraception and a retention in male function can be realized. Kits including one or more of these implants are also contemplated.

DETAILED DESCRIPTION OF THE PREFERRED EMBODIMENTS

Figure 1:
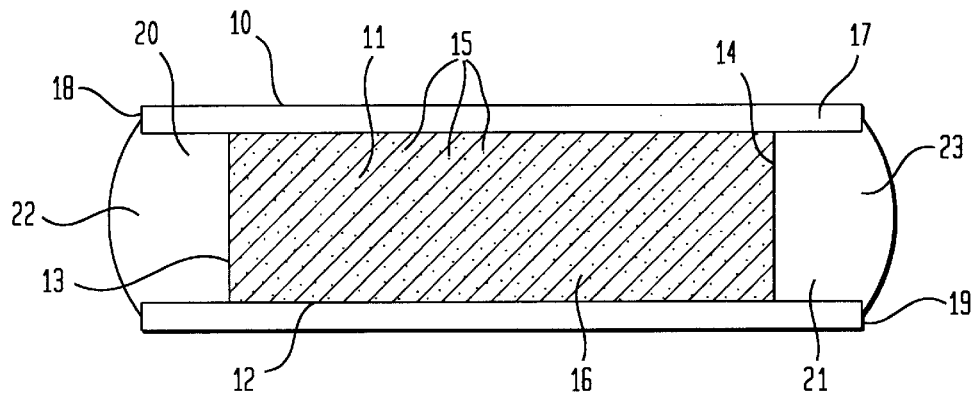
FIG. 1 is a cross sectional view of the implant of the present invention.

The term "androgen" as used in accordance with the present invention encompasses male sex hormones, both naturally occurring and synthetic. The androgenic hormones are steroids which are produced in the body by the testis, in the cortex of the adrenal gland or in the laboratory. These include testosterone and its esters, buciclate, cypionate, propionate, phenylpropionate, cyclopentylpropionate, isocarporate, enanthate and decanoate. Synthetic androgens such as MENT and its esters such as MENT Ac are also encompassed by the term.

The implant of the present invention may also be used to deliver functionally related compounds such as anabolic agents. These agents generally exhibit strong anabolic potency and relatively weaker androgenic activity. These compounds include methandriol, oxymetholone, methandienone, oxymesterone, nondrolone phenylpropionate and norethandrolone. The esters of all of the above compounds are preferred. For the purposes of the present invention, these compounds can also be considered androgens.

Androgen containing subcutaneous implants in accordance with the present invention may be used alone for therapeutic protocols involving the administration of androgens such as the treatment of hypogonadism, prostatic hyperplasia and muscle wasting. The implantable androgen delivery device in accordance with the present invention is designed to include sufficient androgen so as to provide the subject or patient with a required daily dose of a pharmaceutically effective amount of the androgen over the functional useful life of the implant. This should preferably be at least 7 days and more preferably 30 days or longer.

Implants capable of delivering androgen evenly over 100 to 180 days are particularly preferred. Also, preferably, the rate at which androgen is provided to the patient is relatively constant, i.e., a zero order or pseudo-zero order release profile.

The core of these androgen containing implants are composed of silicone elastomers and drug. A broad class of silicone elastomers can be used to form the silicone-elastomer drug matrix. Suitable silicone elastomers in accordance with the present invention include SILASTIC® and R-2602 RTV silicone elastomer available from Nusil Silicone Technology, 1040 Cindy Lane, Carpinteria, Calif. 93013. The silicone elastomers can be catalyzed so that polymerization and formation of the core is accomplished at room-temperature. The core may also be formed by heat curable core material.

The membrane or coating is preferably made of an EVA polymer. The melt index of this membrane material is less than 10 gl/10 min., and preferably less than or equal to 8 g/10 min. More preferably, the melt index is less than about 5 g/10 min. and most preferably about 4 g/10 min. The vinyl acetate ("VA") content is generally less than 20% by weight. The EVA copolymer could have, for example, a composition of about 9–12% VA polymer content.

Suitable EVA polymers which can be used as a membrane are, for example, Evatane® with the designations 501/502 (melt index 2, vinyl acetate content 7.55%), 554/555 4, (12.5%), 540 (10, 18%) and particularly 571 (8, 15%), Elvax® with the designations 450, 460, 470, 550, 560, 650, 660, 670, 750, 760 and 770, and Evatane® 1080 VN 5 and in particular 1040 VN 4 supplied by Atochem.

Figure 2:
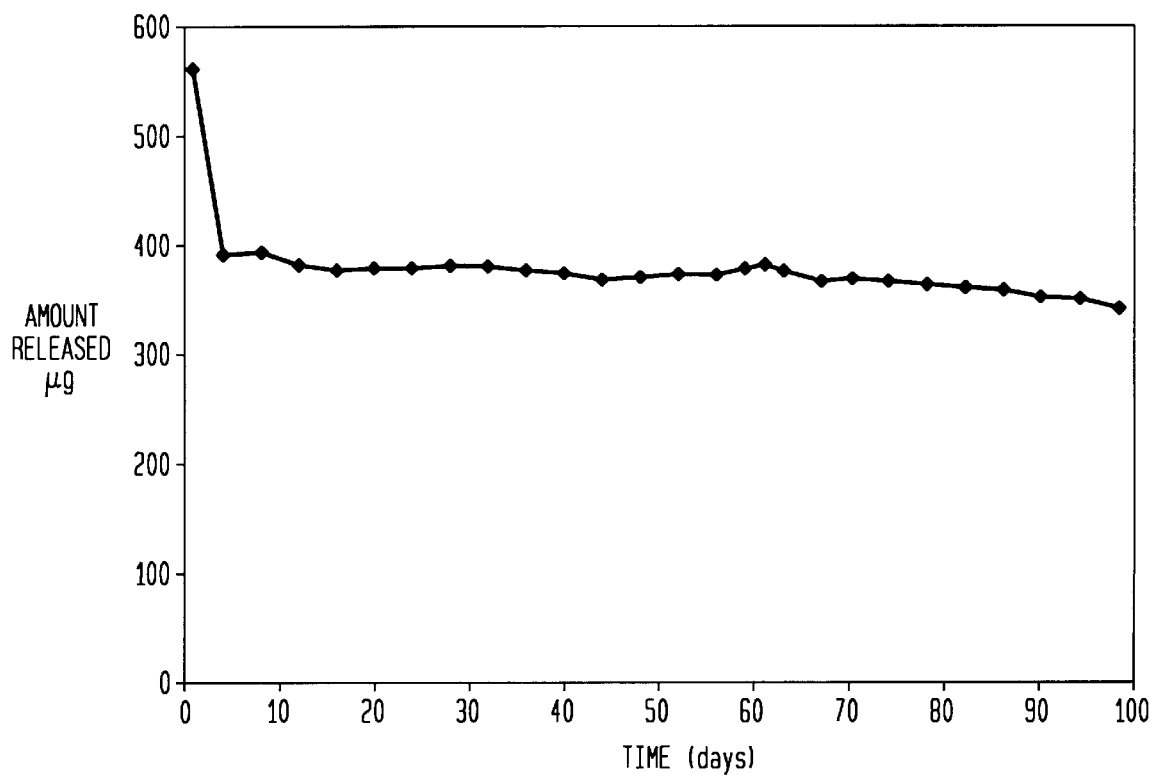
FIG. 2 is a graph showing the in vitro release profile of MENT Ac from 60% MENT Ac-silicone elastomer matrix cores covered with an EVA tubing as illustrated in FIG. 1.
Figure 3:
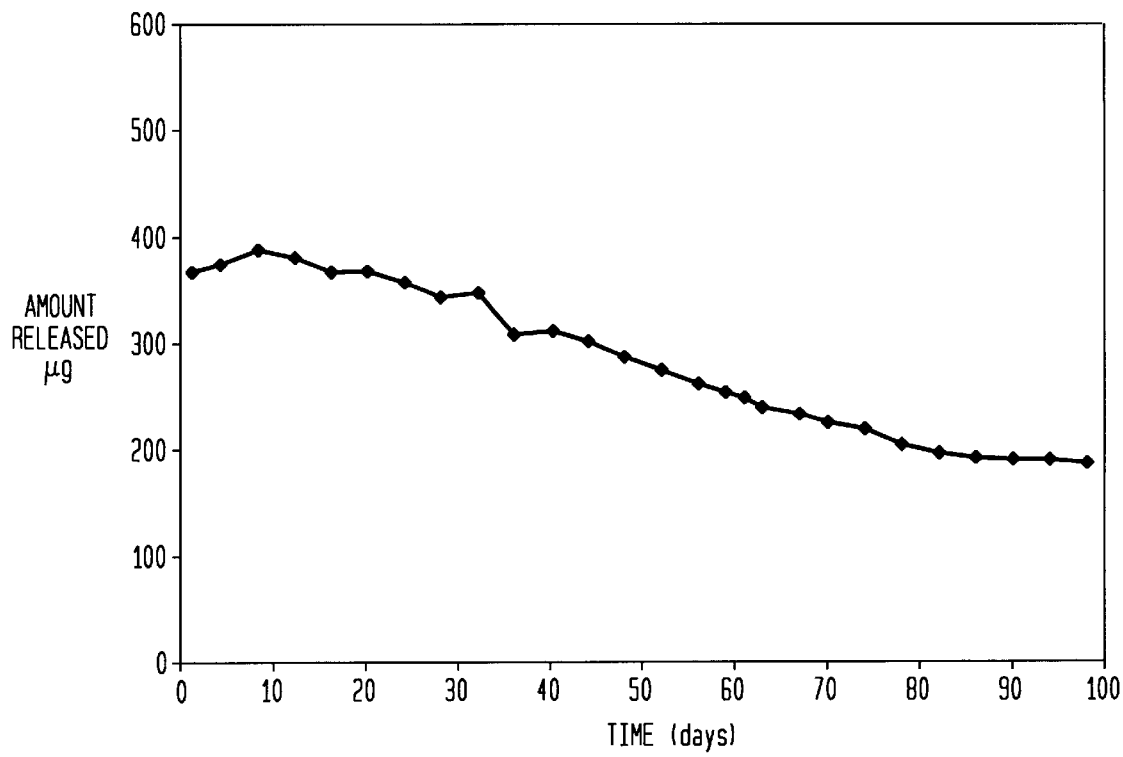
FIG. 3 is a graph showing the in vitro release rate profile of MENT Ac from 60% MENT Ac-EVA matrix cores with an EVA tubing.

While the EVA membrane or coating is rate-limiting, the core material also has an effect on the drug release rate profile of the implant. FIG. 2 illustrates the in vitro release profile of MENT Ac from an implant containing a silicone elastomer-drug matrix surrounded by an EVA tubing in accordance with the present invention. FIG. 3., on the other hand, illustrates the in vitro release profile of MENT Ac from an implant containing and EVA-drug matrix surrounded by an EVA tubing.

The implants of FIGS. 2 and 3 were manufactured in a similar fashion. In both cases, the core matrices were made by extruding 60% MENT Ac/matrix material into molds. Preparation of the silicone elastomeric core/EVA membrane implants in accordance with FIG. 2 was performed in the following manner: 1.5 g of MENT Ac was mixed with 1 g of R-2602 RTV Silicone Elastomer (Nusil Silicone Technology, 1040 Cindy Lane, Carpinteria, Calif. 93013). 2–3 drops of Stannous Octoate were introduced and thoroughly mixed. The mixed paste was filled into a metallic syringe and injected into a brass mold with lumens with appropriate diameter, for example, 2.38 mm. The paste mixture could be directly (in the open air) extruded through a nozzle of a certain diameter, but injecting into a mold ensures the uniformity of the diameter of the obtained core rods. The drug mixture was allowed to be polymerized at room temperature and the mold was opened after curing at 80° C. for 10 minutes. The obtained rods were cut into 4 cm pieces.

EVA tubing (9% VA content, about 2.55 mm in diameter) was cut into 5 cm lengths. The tubing has wall thickness of from about 0.14 mm to about 0.17 mm. The tubing were soaked in methylene chloride for about 1 minute.

Each of the 4 cm rods was introduced into the lumen of one of the 5 cm pieces of the soaked EVA tubing, leaving about 0.5 cm unfilled at both sides. The filled tubing was left overnight at room temperature to allow for the evaporation of methylene chloride. The two ends of the tubing were then sealed by filling with melted EVA (25% VA content).

The sealed implants were heated at 70° C. for 5–10 minutes to enhance the sealing and the adherence between the outside EVA tubing and the end seals. The two ends of the filled tubing were trimmed, leaving about 2.5 mm as a sealing tip. The obtained implants could be suitably sterilized and packaged. Indeed, these implants were made as described in Example 1.

Preparation of the EVA core/EVA membrane implants in accordance with FIG. 3. was performed in the same fashion as the implants of FIG. 2 except that the core material was constructed in the following manner: 1 g of EVA pellets, 25% VA content, (Aldrich Chemical Company Inc., CRAFTSMEN IN CHEMISTRY MILWAUKEE Wis. 53233 USA) was soaked in 12 ml of methylene chloride (Fisher Scientific).

The obtained solution was vortexed before and after the addition of 1.5 g of MENT Ac. Methylene chloride was evaporated under vacuum (at room temperature) for 2 hours. The obtained solid dispersion was filled into a metallic syringe and heated to 110° C. of 5 minutes and then extruded through the 0.1 inch nozzle of the metallic syringe into appropriate molds. The obtained rod was cooled and cut down into 4 cm pieces.

Each of the 4 cm rods was then introduced into the lumen of one of the 5 cm pieces of the soaked EVA tubing, leaving about 0.5 cm unfilled at both sides. The filled tubing was left overnight at room temperature to allow for the evaporation of methylene chloride. The two ends of the tubing were then sealed by filling with melted EVA (25% VA content).

The sealed implants were heated at 70° C. for 5–10 minutes to enhance the sealing and the adherence between the outside EVA tubing and the end seals. The two ends of the filled tubing were trimmed, leaving about 2.5 mm as a sealing tip. The obtained implants could be suitably sterilized and packaged.

Measurement of the in vitro diffusion of MENT Ac implants of FIGS. 2 and 3 was carried out by: a. gluing each implant above the bottom of individual glass vials (about 25 ml capacity) using Medical Adhesive; b. quantitatively measuring 20 ml of 1:750 ZEPHIRAN® solution, available from Winthrope Labs, a division of Sterling (Benzalkonium chloride solution supplied in a 17% aqueous solution) into each of the vials; c. screwing the cap to the vial and placing it in a horizontal position in the appropriate rack in the water bath; d. adjusting the temperature to 37±1° C. and shaking speed to 100±2 strokes per minute; e. changing solutions daily, and continuing to incubate; and f. assaying samples daily using UV spectrophotometer at the appropriate wave length (243 nm). ZEPHIRAN® solution is used as a reference standard.

Figure 4:
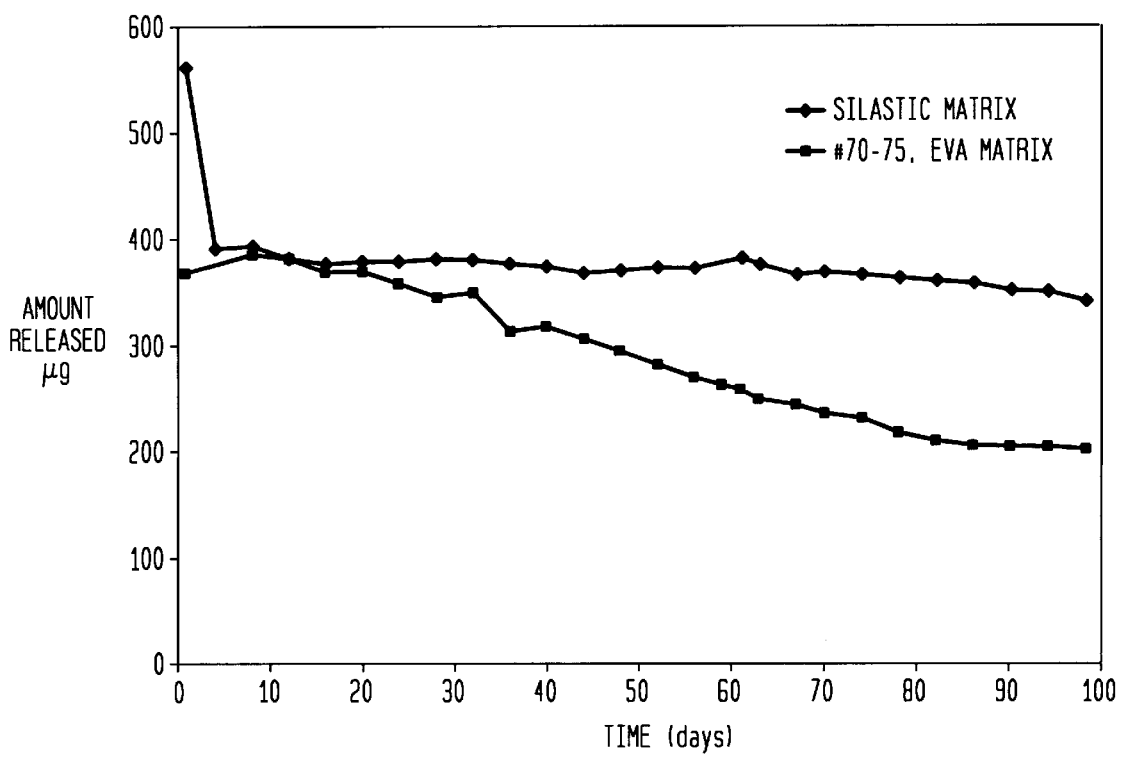
FIG. 4 is a graph showing comparison of the release rates of MENT Ac from two implants, one with a SILASTIC-MENT Ac matrix core and the other with an EVA core. Both are encased in an EVA membrane.

As illustrated in FIG. 2, following an initial burst of the drug, the silicone elastomeric drug matrix implant exhibited a pseudo-zero-order release rate profile over the entire 100 day period. By contrast, the release rate profile of the EVA-based implant was less uniform over the 100 day period (FIG. 3). This comparison is further depicted in FIG. 4 which shows a side by side comparison of the release rates profiles of the silicone elastomeric-drug matrix and EVA-drug matrix implants.

Without limitation, the better release rate profile of an implant having a silicone elastomeric-drug matrix as compared with an EVA copolymer drug matrix may be based on the solubility properties of the steroid in the drug matrices. In the EVA co-polymer drug matrix implant, the matrix is made of polyethylene and vinyl acetate. The steroid is only soluble in the vinyl acetate moiety of the EVA polymer. The EVA drug matrix contains areas of crystallinity through which the steroid cannot diffuse and amorphous areas through which the steroid can diffuse. By contrast, in implants containing a silicone elastomeric matrix, the steroid is soluble in the entire matrix and thus more uniformly reaches the EVA rate-limiting outer tubing. This is particularly surprising in view of the advance which the EVA core/EVA coated implant represented over silicone core/silicone coated implants used in female contraceptives. See U.S. Pat. No. 5,733,565.

FIG. 1 illustrates a longitudinal cross sectional view of a partially assembled implant 10 which contains a central core 11 extending in an axial direction and having an outer surface 12 and opposing ends 13 and 14. The central core 11 is a matrix of a pharmaceutically effective amount of subdermally administerable androgen 15 substantially uniformly dispersed in a silicone elastomer base 16 so as to form a matrix. Membrane 17 overlies the core 11. Membrane 17 is made of an EVA polymer. Membrane 17 has opposed ends 18 and 19 which extend axially beyond opposing ends 13 and 14, respectively, of central core 11 to define cavities 20 and 21, respectively. Upon complete assembly of the device, cavities 20 and 21 are substantially filled with ethylene vinyl acetate copolymer (EVA), with a 25% vinyl acetate content, forming seals 22 and 23. Seals 22 and 23 disposed, in cavities 20 and 21, respectively, cooperate with the overlying ends 18 and 19, respectively, of membrane 17 to completely encapsulate central core 11. The seals 22 and 23 can be made of same EVA material which forms the cavities and membrane of the implant. The EVA copolymer of the seals could have, for example, a composition of about 9%–25% VA polymer content. Preferably the VA content of the seals is 9%. The sealant minimizes the diffusion of the drug in the axially direction, i.e., from the ends of the device. The potential for undesirable axially diffusion of the drug increases as the length of the implant decreases, e.g., to about 3.0 centimeters and less. The seals 22 and 23 also serve to more securely hold the device together, e.g., maintain the structural integrity of the device, and prevent the infiltration of the biological tissues into the otherwise open ends of the device.

An androgen containing implant is preferably cylindrical with a maximum external diameter of about 3.0 millimeters and a maximum length of about 5.0 centimeters. More preferably, the implants will have an external diameter ranging from between about 2.4 to about 2.7 millimeters and a length of between about 4.4 to about 5.0 centimeters. The rod-shaped core, in this case, ranges from between about 4.0 to about 4.5 cm in length. The rod's diameter is obviously sufficient to fit within the tubing. Of course, depending upon the circumstances, it may be necessary or desirable to increase the length or diameter of the device or to change it from a cylindrical configuration to a different geometry. In this regard, other geometric shapes, including, for example, rings, loops, and discs, are contemplated for the present invention. However, as it is necessary to produce the device in such a way as not to cause an impediment or to cause discomfort to the user, it is preferable to keep it as small and unobtrusive as possible.

The subdermal implantable androgen delivery device in accordance with the present invention can generally be fabricated in accordance with standard techniques. The androgen or androgens of choice are mixed with the silicone elastomer so as to form a homogeneous matrix. Mixing is continued until a substantially uniform dispersion is realized. The material is then processed to the desired shape by molding, casting, extrusion or other appropriate processes. An outer layer can then be applied to the central core in a variety of ways, such as by mechanical stretching, swelling or dipping. See, for example, U.S. Pat. Nos. 3,832,252, 3,854,480 and 4,957,119, the text of which are hereby incorporated by reference. See also the discussion of the construction of androgen containing implants in U.S. Pat. No. 5,733,565, the text of which is also hereby incorporated by reference.

In a preferred method, the androgen is mixed with the silicone elastomer and mixed uniformly to give a paste. An appropriate amount of a catalyst such as, for example, Stannous Octoate is introduced and mixed quickly and thoroughly throughout the material. The mixture is filled into a metallic syringe or an extruder and injected through a suitable mold. The extruded core material could be left to cure at room temperature or could be cured in an oven at moderate temperature such as 80–90° C. Individual cores or rods can then be cut from the extruded material to any desired length. The dimensions of each rod or core are determined, at least in part, based on the implantation method and location, the intended useful life, the composition of the SILASTIC® material, the amount of androgen and its potency, etc.

The core is then covered with a rate-limiting membrane of an EVA polymer. As previously noted, this can be done by a number of known processes including, for example, spraying or dipping the core in the coating material. However, one of the more convenient ways of accomplishing same is by providing a piece of EVA tubing of sufficient internal and external diameter composed of the desired rate-limiting material. This tubing is cut into pieces which are slightly longer than the length of the rods or cores. The tubing is then soaked in an organic solvent such as methane chloride for a brief time (on the order of 60 seconds). The core is then introduced into the lumen of the EVA tubing, leaving about 0.5 centimeters of unfilled tubing at both ends. The tubing preferably has an outside diameter of 2.39 to 2.55 millimeters and an inside diameter or lumen of 2.13 to 2.36 millimeters. The filled tubing is then dried. The two ends of the tubing are then sealed with filling with a melted EVA. The sealed implants may then be heated briefly to enhance the seal and the adherence between the EVA tubing and the end seals. This will also ensure evaporation of any traces of organic solvent, if any. The two ends of the implant are then trimmed, leaving about 2.5 millimeters as a sealing tip. The ends of the device can also be sealed in a variety of other ways in accordance with art-recognized techniques. For example, radio frequency can be used. The thus obtained implants can then be sterilized using, for example, ethylene oxide and packaged for use. The device could also be produced by coaxial extrusion as is well known in the art.

The implant of the invention should contain a quantity of androgen which is sufficient to provide for the required daily dose of a pharmaceutically effective amount of that androgen over a desired period of time. This means that if the appropriate daily dose of androgen is 5 micrograms per day, then the implant should contain sufficient androgen to allow for the administration of 5 micrograms every day for as long as the implant is used. Preferably, the implant has a useful life, of at least seven days. Most preferably, the subcutaneous implant will deliver a reasonably constant amount of androgen over a period of at least 30 days.

Implants which can deliver a steady daily amount of androgen over 100 to 180 days or more are preferable. As previously noted, the implant should be designed to insure as near a zero-order release profile of androgen over the useful life as possible. A pseudo-zero-order release profile (following the initial burst is illustrated in FIG. 2). An "pharmaceutically effective" amount of androgen is that amount sufficient to support the sexual function (when used in combination with a male infertility implant, vaccine, or other drug leading to suppression of testosterone) for the predetermined period of time, e.g., the useful life of the implant. The weight ratio of the silicone elastomer based material to the androgen in the central core will generally range from between about 1:1 to about 1:1.5. The implant of the present invention should contain a sufficient quantity of androgen to provide a substantially constant release of a daily dose of from between about 100 to about 1,000 micrograms of androgen and more preferably between about 200 and about 500 micrograms of androgen each day over the useful life of the implant. Preferably, the core consists of between 50% to about 70% by weight of androgen and from between about 50% to about 30% by weight of a silicone elastomer.

Sterilants are drugs which kill sperm, interrupt sperm production, suppresses sperm production, or render sperm unable to fertilize an egg. The effects of these sterilants are generally reversible. That is, once they are removed, sperm production and/or viability return. A preferred subclass of sterilants used in accordance with the present invention is LHRH (luteinizing hormone-releasing hormone)peptides as well their analogs and functionally similar compounds. These compounds are active polypeptides which act on the anterior pituitary gland to effect release of hormones that affect the activity of reproductive organs. Naturally occurring LHRH peptide is produced in the hypothalamic region of the brain and controls the reproductive cycle of mammals by acting to effect the release of luteinizing hormone and follicular stimulating hormone which in turn acts on the gonads to stimulate the synthesis of steroid hormones and to stimulate gamete maturation. LHRH can be used for hypogonadal conditions and impotence and for stimulating spermatogenesis, and androgen production in the male. Large doses of highly potent and long lasting analogs of LHRH have the opposite effect; suppressing spermatogenesis in the male. Thus, this material can act as a chemical sterilant. See U.S. Pat. Nos. 4,234,571, 5,292,515 and 5,266,325. Other LHRH analogs are known which provide, at lower dose levels, chemical sterilant activity in males as well.

In accordance with the present invention these sterilant compounds may be administered through a second implant which differs significantly in its structure and composition when compared to the first androgen delivering implant. One group of delivery implants useful as the second implant in accordance with the present invention is a hydrogel implant. Hydrogel based delivery systems for LHRH and its analogs are known and are described in U.S. Pat. Nos. 5,266,325 and 5,292,515, the texts and drawings of which are hereby incorporated by reference.

In one embodiment, the second implant is formed from a homogeneous hydrophilic copolymer having a predetermined equilibrium water content or "EWC" value. This material can be produced by the addition polymerization of a mixture containing ethylenically unsaturated hydrophilic monomer A and an ethylenically unsaturated hydrophilic monomer B copolymerizable therewith. The copolymer is useful as a hydrogel membrane in the diffusion therethrough of a selected active compound, (sterilant), in an aqueous, or non-aqueous medium, at a predetermined rate.

The second implant is preferably a uniform, homogeneous, water-insoluble, water-swellable copolymeric, cylindrically-shaped article with a concentric core having a predetermined equilibrium water content value. The implant is formed by the addition polymerization of a mixture containing ethylenically unsaturated hydrophilic monomer A and ethylenically unsaturated monomer B copolymerizable therewith. This can provide an implantable device which is useful for the sustained release of an active agent therefrom to a patient. This embodiment involves: a. forming a polymerizable liquid mixture containing monomer A and monomer B in amounts sufficient to yield a homogeneous copolymer AB having a predetermined equilibrium water content value; b. introducing into the open end of a polymerization column a predetermined amount of said polymerizable liquid mixture; c. rotating said polymerization column about its longitudinal axis maintained substantially parallel to the ground at a speed sufficient to cause radially outward displacement of said polymerizable liquid mixture to assume a predetermined hollow cylindrical liquid configuration within said column; d. maintaining the polymerization column under polymerization conditions to convert said polymerizable mixture of predetermined liquid configuration into a predetermined solid hollow cylindrical configuration; and e. recovering a copolymeric cylindrically-shaped article having the predetermined equilibrium water content value and further characterized by a cylindrical core or reservoir and smooth internal and external cylindrical surfaces of substantially uniform thickness between said surfaces. In a preferred embodiment, a homogenous hydrophilic copolymer of 2-hydroxyethyl methacrylate ("HEMA") and hydroxypropyl methacrylate ("HPMA") are produced and used.

In one embodiment, the second implant is a uniform, cylindrically-shaped copolymeric cartridge characterized by a predetermined EWC value, produced with a substantial uniformity of thickness between its outer and inner cylindrical surfaces using a pore-forming agent uniformly or homogeneously distributed throughout the cartridge. In this aspect of the invention, a uniform or homogeneous polymerizable liquid mixture of monomer A, monomer B, and a pore-forming agent, is prepared using amounts sufficient to result in a homogeneous copolymer having the targeted EWC value.

Another embodiment of the second implant involves the preparation of a delivery device for the delayed/sustained release of an active agent therefrom e.g., a drug, which comprises: a. introducing active agent and, optionally, a pharmaceutically acceptable carrier, into the core (reservoir) of the aforesaid cylindrically shaped copolymeric body in an amount sufficient for extended sustained release of said active agent into a delivery environment; b. further introducing polymerizable liquid material into the said core in an amount sufficient to cover the active agent or to substantially or completely fill the core to the top of the cylindrical body, said polymerizable liquid material in its polymerized state having an equilibrium water content value which exceeds the equilibrium water content value of the cylindrical body; and c. polymerizing said polymerizable material to effectively seal the core opening with a plug (layer) of water-swellable, water-insoluble polymer.

The delayed/sustained release implant comprises a hydrophilic copolymeric cartridge of xerogel or hydrogel (collectively referred to as a hydrogel herein). The implant also includes a hydrophilic sealing means to seal the open end of the cartridge thereby defining an enclosed core, a sterilant and optionally, a pharmaceutically acceptable carrier, contained in the core in an amount sufficient to be continually released over an extended period of time. The cartridge is characterized by water-swellability, water-insolubility, smooth, unscored outer and inner cylindrical surfaces, and a predetermined EWC value. The hydrophilic sealing means exhibits water-swellability, water-insolubility, and an equilibrium water content value which exceeds that of the cartridge.

Figure 5:
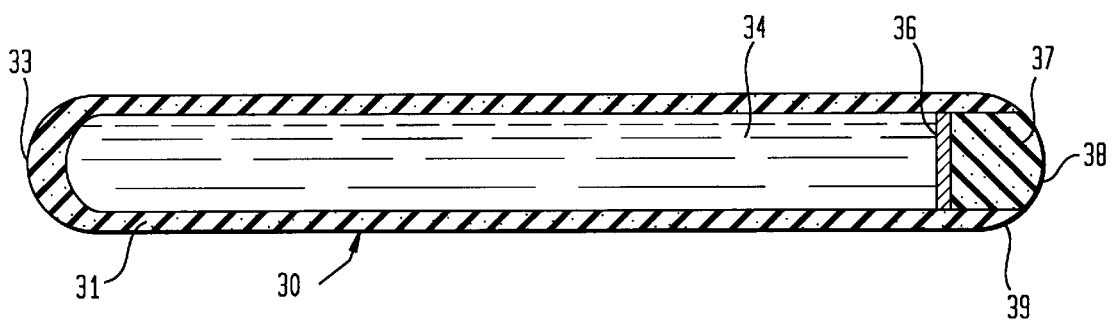
FIG. 5 is a cross-sectional view of an implant designed for the administration of LHRH.

FIG. 5 illustrates one form of the second implant 30 of the invention. Cartridge 31 is shown with an oval-like base 33 (after trimming and polishing) packed with drug such as LHRH analogs 34 in its core. The external and internal cylindrical services of cartridge 30 are smooth and unscored. Teflon covered 36 separates drug 34 from hydrophilic plug 37, formed in situ from liquid material and polymerized to a solid hydrophilic plug 37. The equilibrium water content of plug 37 and thus its swellability are greater than the EWC of cartridge 31. Therefore, a hermetical seal will be formed upon hydration. The outer surface 38 of plug 37 including a portion of the contiguous cartridge wall 39 has been oval shaped by trimming and polishing.

The amount of LHRH or its analogs will depend on many factors. However, principally, the amount will depend upon the rate and extent of release, the useful life of the implant, the physical size and needs of the patient, the type of treatment for which the implants are prescribed and, of course, the need to complement the administration of androgen from the first implant previously described. Treatment of infertility with synthetic LHRH peptides requires a low level of drug, while reduction of fertility and related effects requires a large dose relative to the activity of naturally occurring LHRH. For LHRH agonist fertility control, it is desired to release the drug at such a rate that the subject will receive between 0.05 and about 100 micrograms per kilogram of body weight per day, preferably between 0.1 and 5.0 micrograms per kilogram body per day.

The result is a second implant for sustained release of an active agent such as this sterilant therefrom which includes a biocompatible, non-biodegradable, water-swellable, water-insoluble, hydrophilic cartridge of an AB copolymer, a sealant for closure of the open end of the cartridge which includes a plug of biocompatible non-biodegradable, water-swellable, water-insoluble hydrophilic polymer having an equilibrium water content value greater than that of the cartridge per se. The sterilant, either alone or in combination with other carriers, diluents or active ingredients, is contained in the reservoir of the cartridge in an amount sufficient to provide the predetermined sustained release thereof over the useful life of the implant. Most preferably, the copolymer AB consists of from about 25 to 70 weight percent of 2-hydroxy ethyl methacrylate (monomer A) units and from 75 to 30 weight percent of monomer B units. The B units possess predetermined EWC value in the range of 25 to about 75 weight percent. The monomer B can be hydroxy propyl methacrylate units.

In an embodiment, the two implants may be provided to the attending physician in a single kit, ready for use. The kit would include two implants, one for the delivery of an androgen and one for delivering a sterilant. Preferably, at least one of the implants will already be loaded into one a device capable of administering the implant directly to the patient. For example, each could be separately loaded into a syringe or trocar for subcutaneous administration. Most preferably, the second implant will be hydrated in saline and stored in hypertonic saline.

The kit may also include gauze, trocars, scalpels and the like, all in a sterilized container. The first implant can be sterilized by use of ethylene oxide. However, the second implant is preferably sterilized by steam.

However, it will often be beneficial to administer the first and the second implants at different times. For example, the second implant would be implanted first, with the first implant containing the androgen being implanted when the testosterone levels become significantly depressed (about castration levels). This may occur weeks later. Of course, both implants may still have been provided in a single kit. However, individual kits, designed to be mixed and matched may be provided for each implant.

Of course, the present invention is not limited to a system which uses a hydrogel implant as described herein for the second implant. Any implant which is capable of delivering one or more sterilants in a manner which is complementary to the first implant previously described may be used.

When provided as part of an implantable system comprising a first implant designed for the administration of androgen and a second implant intended for the administration of a sterilant, the first and second implants are preferably cooperatively sized and shaped and are designed such that each releases a pharmaceutically complementary amount of androgen and sterilant respectively. This means that the two implants may be administered in proximity with one another. Therefore, they should be sized such that they will not in any way cause interference with one another or discomfort to the patient. In addition, the two implants should be designed such that the amount of androgen and amount of sterilant provided each day to the patient will be both effective in terms of contraception and in terms of maintaining sexual function. The sterilant (LHRH agonist) is provided in an amount of about 50–120 mg/day. The androgen (MENT Ac) is provided in an amount of about 100–1000 mg/day and more preferably in amounts of about 200–800 mg/day. Even more preferably, androgen is provided in an amount of 300–700 mg/day, and most preferably 400–600 mg/day.

In vitro diffusion of either androgen, from the first implant or the diffusion of the sterilant from the second implant is an indication of the diffusion characteristics of the implants in vivo. In vitro diffusion of the drug from either the first or the second implant may be determined, for example by the methods disclosed in Chien et al., *J. Pharm. Sci.*, 63,365 (1974), or by the methods described in U.S. Pat. No. 3,710,795. In vivo diffusion can be measured by, for example, the methods described in Sundaram et aL, "7 Alpha-Methyl-19-Nortestosterone(MENT): The Optimal Androgen For Male Contraception", *Annals of Medicine*, (1993), 25, 199–205.

The devices of the present invention can be implanted into a subject in accordance with standard procedures. By the term "subject" it is meant mammals, e.g., humans, valuable domestic household, sport or farm animals, the laboratory animals. In the case of these implants, for example, this procedure is advantageously performed with a trocar and the device is preferably implanted beneath the skin of the upper arm of the patient. See Shoupe et al., Am. J. Obstet. Gynecol., 160:1286–92 (1989), and Tikkanen et al., J. Reprod. Med., 31:898–905 (1986).

EXAMPLES

Example 1
Preparation of MENT Ac/Silicone Elastomer Implant

A. Preparation of Core Rods Containing 60% w/w MENT Ac 1.5 g of MENT Ac was mixed with 1 g of R-2602 RTV Silicone Elastomer (Nusil Silicone Technology, 1040 Cindy Lane, Carpinteria, Calif. 93013). 2–3 drops of Stannous Octoate were introduced and thoroughly mixed. The mixed paste was filled into a metallic syringe and injected into a brass mold with lumens with appropriate diameter, for example, 2.38 mm. The paste mixture could be directly (in the open air) extruded through a nozzle of a certain diameter, but injecting into a mold ensures the uniformity of the diameter of the obtained core rods. The mold was opened after curing at 80° C. for 10 minutes. The rods were either cut into 4 cm pieces or were injected directly into a mold of the required diameter and length of 4 cm.

B. Encasing of the Rods With EVA Tubing

EVA tubing (9% VA content, about 2.55 mm in diameter) was cut into 5 cm lengths. The tubing has wall thickness of from about 0.14 mm to about 0.17 mm. The tubing were soaked in methylene chloride for about 1 minute.

Each of the 4 cm rods was introduced into the lumen of one of the 5 cm pieces of the soaked EVA tubing, leaving about 0.5 cm unfilled at both sides. The filled tubing was left overnight at room temperature to allow for the evaporation of methylene chloride. The two ends of the tubing were then sealed by filling with melted EVA (25% VA content).

The sealed implants were heated at 70° C. for 5–10 minutes to enhance the sealing and the adherence between the outside EVA tubing and the end seals. The two ends of the filled tubing were trimmed, leaving about 2.5 mm as a sealing tip. The obtained implants could be suitably sterilized and packaged. The implants used in FIGS. 2 and 4 were prepared in accordance with the foregoing example.

We claim:

1. An implantable system, comprising: a first implant intended for subcutaneous or local administration of an androgen, said first implant including an androgen selected from a group consisting of 7α-methyl-19-nortestosterone, 7α-methyl-19-nortestosterone acetate, testosterone, esters of testosterone, methandroil, oxymetholone, methandienone, oxymesterone, nondrolone phenylpropionate and norethandrolone, in an amount which is sufficient to provide the daily dose of a pharmaceutically effective amount of said androgen over a predetermined time dispersed in a core formed of a silicone elastomer, and a membrane encasing said core, said membrane formed of an ethylene vinyl acetate copolymer; and a second implant intended for subcutaneous or local administration of a sterilant, said second implant including said sterilant in an amount sufficient to provide for the daily dose of a pharmaceutically effective amount of said sterilant over said predetermined time.

2. The implantable system of claim 1, wherein said first implant and said second implant are of a cooperative size and shape and are designed such that each releases a pharmaceutically complementary amount of said androgen and said sterilant, so as to provide treatment to a patient in need thereof.

3. The implantable system of claim 1, wherein said ethylene vinyl acetate copolymer of said first implant has a molecular weight such that the melt index is greater than 10 grams/10 minutes, and a vinyl acetate content less than 20% by weight.

4. The implantable system of claim 1, wherein said androgen is MENT.

5. The implantable system of claim 4, wherein said androgen is MENT Ac.

6. The implantable system of claim 1, wherein said pharmaceutically effective amount of said androgen is provided in an amount which is sufficient to provide for the required daily dose of a pharmaceutically effective amount of said androgen over a predetermined time of at least about 7 days.

7. The implantable system of claim 1, wherein said predetermined time is at least about 100 days.

8. The implantable system of claim 7, wherein said predetermined time is at least about 180 days.

9. The implantable system of claim 1, wherein said androgen is provided in an amount which is sufficient to provide a daily dose of between about 100 and about 1000 micrograms of androgen per day.

10. The implantable system of claim 9, wherein said androgen is provided in an amount which is sufficient to provide a daily dose of between about 200 and about 500 micrograms of androgen per day.

11. The implantable system of claim 1, wherein said core of said first implant consists of from about 50 to about 75% androgen and from about 50 to about 25% of said silicone elastomer.

12. The implantable system of claim 1, wherein said second implant includes a biocompatible, non-biodegradable, water-swellable, water-insoluble, hydrophilic cartridge of a copolymer AB having from about 25 to about 70 weight percent of 2-hydroxy ethyl methacrylate (monomer A) units and from about 75 to about 30 weight percent of monomer B units and possessing a predetermined EWC value in the range of from about 25 to about 75 weight percent;

a sealant for closure of an open-end of said cartridge comprising a plug of biocompatible, non-biodegradable, water-swellable, water-insoluble, hydrophilic polymer having an equilibrium water content value greater than that of the cartridge;

with said sterilant contained in a reservoir disposed within said cartridge.

13. The implantable system of claim 12, wherein said monomer B includes hydroxypropyl methacrylate units.

14. The implantable system of claim 13, wherein said sterilant is provided in an amount of between about 5 mg and about 50 mg.

15. The implantable system of claim 1, wherein said sterilant is LHRH or an LHRH analog.

16. The implantable system of claim 15, wherein said sterilant is LHRH or an LHRH analog.

17. An implant intended for subcutaneous or local administration comprising:

(a) a drug-polymer matrix core including a silastic elastomer and an androgen selected from a group consisting of 7α-methyl-19-nortestosterone, 7α-methyl-19-nortestosterone acetate, testosterone, esters of testosterone, methandroil, oxymetholone, methandienone, oxymesterone, nondrolone phenylpropionate and noretyhandrolone, in an amount sufficient to provide for the required daily dose of a pharmaceutically effective amount of said androgen over a predetermined time; and (b) a membrane encasing said drug-polymer matrix core and said androgen and said membrane including ethylene vinyl acetate having a molecular weight which results in a melt index which is less than 10 grams/10 minutes and a vinyl acetate content of less than 20% by weight.

18. The implant of claim 17, wherein said androgen is MENT.

19. The implant of claim 17, wherein said androgen is MENT Ac.

20. The implant of claim 17, wherein said pharmaceutically effective amount of said androgen is provided in an amount sufficient to provide for the required daily dose of a pharmaceutically effective amount of said androgen over a predetermined time of at least 7 days.

21. The implant of claim 20, wherein said predetermined time is at least about 30 days.

* * * * *